United States Patent [19]

Hancock, II et al.

[11] 4,034,005
[45] July 5, 1977

[54] PROCESS FOR MAKING AROMATIC ACIDS

[75] Inventors: Allen W. Hancock, II, Media; William D. Vanderwerff, West Chester, both of Pa.

[73] Assignee: Sun Ventures, Inc., St. Davids, Pa.

[22] Filed: June 17, 1975

[21] Appl. No.: 587,756

[52] U.S. Cl. .................... 260/515 P; 260/515 R
[51] Int. Cl.² ................ C07C 63/14; C07C 63/06
[58] Field of Search ........ 260/515 R, 515 P, 514 G

[56] References Cited

UNITED STATES PATENTS

| | | | |
|---|---|---|---|
| 3,031,500 | 4/1962 | Gasson et al. | 260/515 P |
| 3,113,964 | 12/1963 | Farkas et al. | 260/515 P |
| 3,781,343 | 12/1973 | Norton | 260/515 P |

OTHER PUBLICATIONS

Weissberger, Distillation, Technique of Organic Chem., vol. 4, Interscience Pub. Inc., N.Y., N.Y., pp. 175-178 (1951).
Weissberger, Distillation, Technique of Organic Chem., vol. 4, Interscience Pub. Inc. N.Y., N.Y., pp. 712-713 (1965).
Weissberger, Separation & Purification, pt.1, Interscience Pub. Inc., N.Y., N.Y., pp. 719-722 (1956).

Primary Examiner—James O. Thomas, Jr.
Assistant Examiner—G. T. Breitenstein
Attorney, Agent, or Firm—Donald R. Johnson; J. Edward Hess; Paul Lipsitz

[57] ABSTRACT

A process for making an aromatic carboxylic acid of high purity by feeding an essentially equilibrium hydrolysis mixture of an aromatic nitrile to a reactive distillation column operated at a temperature of from about 200° C. to about 325° C. at autogenous pressure where the equilibrium mixture is subjected simultaneously to further hydrolysis and distillation of ammonia, removing water vapor and ammonia from the top of the column, subjecting remaining equilibrium hydrolysis mixture to further hydrolysis and distillation in a reboiler, returning vapor from the reboiler to the distillation column, removing an aqueous solution of product acid from the reboiler, cooling said separated solution, separating acid product, and in order to improve product purity, returning the aqueous filtrate from said separated acid product to a lower portion of said column. In one embodiment of the invention the hydrolysis mixture is obtained by subjecting a nitrile from the ammoxidation of an alkyl aromatic compound to aqueous hydrolysis in a closed reactor at about 200° to about 325° C. until an essentially complete equilibrium is obtained.

12 Claims, 4 Drawing Figures

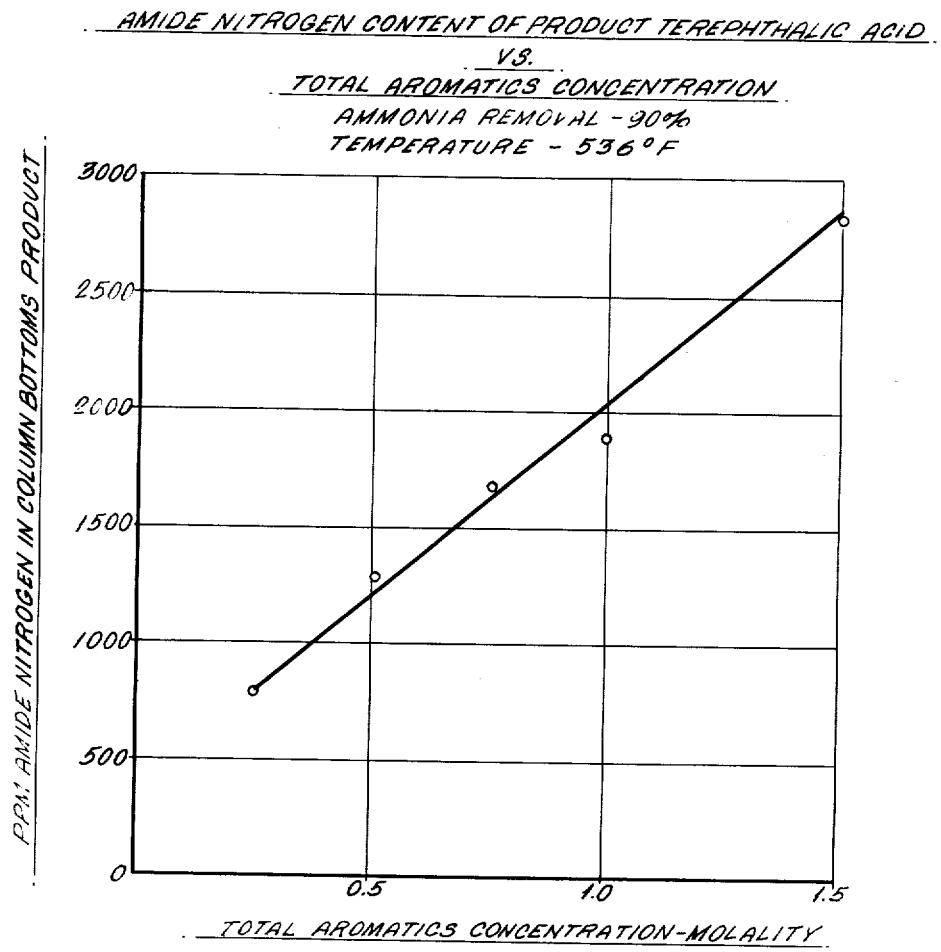

PROCESS FOR MAKING AROMATIC ACIDS

It is known in the art to prepare aromatic carboxylic acids by hydrolysis of the corresponding nitriles which, in turn, are prepared by ammoxidation of alkyl-substituted hydrocarbons. The acids obtained from such processes must generally have high purity and be essentially devoid of nitrogen-containing by-products and, in the case of polycarboxylic acids, must also be free of any by-product monoacids. This is particularly true of aromatic dicarboxylic acids such as terephthalic acid which is the well-known intermediate to polyester fibers. In order to employ terephthalic acid for such use it must have a very high purity and, in particular, be free of nitrogen containing bodies which will discolor the polmer made from such acid, and it must also be free of mono-acids such as p-toluic acid which might arise from incomplete ammoxidation since such a mono-acid would adversely affect polymerization of the acid in that the necessary high molecular weight polymer could not be obtained.

In copending application Ser. No. 565,509 filed Apr. 7, 1975 now abandoned, in the names of Raymond Wynkoop and Allan W. Hancock, II a process for the hydrolysis of aromatic nitriles is disclosed which involves feeding an essentially equilibrium hydrolysis mixture of an aromatic nitrile to a reactive distillation column operated at elevated temperature and at autogenous pressure where the equilibrium mixture is subjected simultaneously to further hydrolysis and distillation of ammonia, removing water vapor and ammonia from the top of the column, subjecting remaining equilibrium hydrolysis mixture to further hydrolysis and distillation in a reboiler, returning vapor from the reboiler to the distillation column, removing an aqueous solution of product acid from the reboiler, cooling said separated solution and separating acid product. It has now been discovered that product purity of the acid obtained in such process can be further improved by maintaining within the system a concentration gradient of the organic materials in the column such that the lower portion of the column is more dilute than the upper portion. While it will be understood that this concentration gradient can be achieved by a variety of means, a preferred technique will be to feed water as diluent, preferably obtained from the aqueous filtrate of the process, to a lower section of the reactive distillation column. Thus, in accord with a preferred embodiment of the invention, a process is provided for making an aromatic carboxylic acid of high purity from the hydrolysate of the corresponding nitrile preferably obtained by ammoxidation of an alkyl aromatic compound, by feeding an essentially equilibrium hydrolysis mixture of an aromatic nitrile to a reactive distillation column operated at a temperature of from about 200° C. to about 325° C. and an autogenous pressure where the equilibrium mixture is subjected simultaneously to further hydrolysis and distillation of ammonia, concentrating ammonia by rectification in the upper portion of the column, removing the concentrated aqueous ammonia vapor from the top of the column, subjecting the remaining equilibrium hydrolysis mixture to further hydrolysis and distillation in a reboiler operated at about 200° to about 325° C., returning vapors from the reboiler to a lower portion of the distillation column, removing an aqueous solution of product from the reboiler, cooling said separated solution, separating acid product and returning the aqueous filtrate from said separated acid product to a lower portion of said column. In another preferred process the nitrile hydrolysate is obtained by an aqueous hydrolysis in a closed reactor at a temperature of from about 200° C. to about 325° C. until an essentially complete hydrolysis equilibrium is reached and the equilibrium hydrolysate is then fed to the reactive distillation unit.

The invention as described above involves a "reactive distillation" and such terminology is used herein to indicate the production of free aromatic carboxylic acid by the efficient removal of ammonia from a reaction zone where the normally equilibrium limited reaction of amide and ammonium salt is shifted to the salt which, in turn, yields, free acid of high purity. Thus, for example, in the hydrolysis of terephthalonitrile in a closed system the chemistry is as follows:

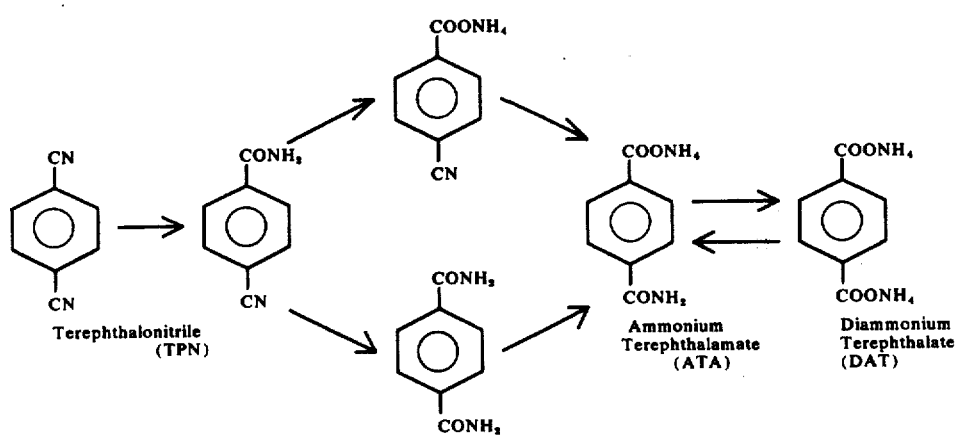

When such a hydrolysis mixture is subjected to reactive distillation the equilibria:

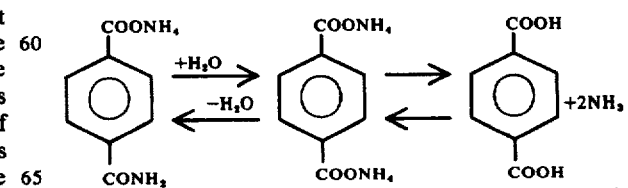

are shifted to the right in the column because ammonia is removed continuously from the reaction zone. Thus, all of the amide nitrogen eventually becomes converted to ammonia and a high purity free acid results as product.

One of the major advantages of the process of this invention is that it enables in a single step:
 a. the concentration of ammonia,
 b. its removal from the system,
 c. elimination of undersired nitrogen impurities and,
 d. the making of high purity free acid. This is to be contrasted with prior art techniques which sweep ammonia from the system without concentration, thus, requiring large volumes of steam. Furthermore, prior art methods yield the ammonium salts as intermediates and require one or more additional steps for conversion to the free acid.

As explained above, an improvement in product purity is achieved by the creation of a concentration gradient within the distillation reactor so that the organic materials are of lower concentration at the bottom as compared to upper portions. This may be the result of a large and unexpected concentration effect on the equilibrium:

where Ar stands for an aromatic entity. The rate and efficiency of ammonia removal and the capital investment and utility costs are all favored by high solution concentration, but product purity appears favored by low concentration. Thus, the process of the invention permits achievement of optimum results in the face of these two conflicting process parameters.

The process of the invention is applicable to the production of a wide variety of aromatic carboxylic acids. The aromatic nitrile starting material may be selected from any of those compounds where one or more nitrile radicals are attached directly to an aromatic ring preferably, a benzene or naphthalene ring. Examples of nitriles falling within this class include benzonitrile, phthalonitrile, isophthalonitrile, terephthalonitrile, the tolunitriles, naphthonitriles such as 1,5- and 2,6-dicyanonaphthalene, and the like. Preferred nitriles for use in the process are those of benzene and naphthalene series such as the phthalonitriles, particularly terephthalonitrile and isophthalonitrile, and 2,6-dicyanonaphthalene.

In the drawings:

FIG. 4 is a graphical illustration of the relationship of product purity to aromatics concentration.

Figure 1:
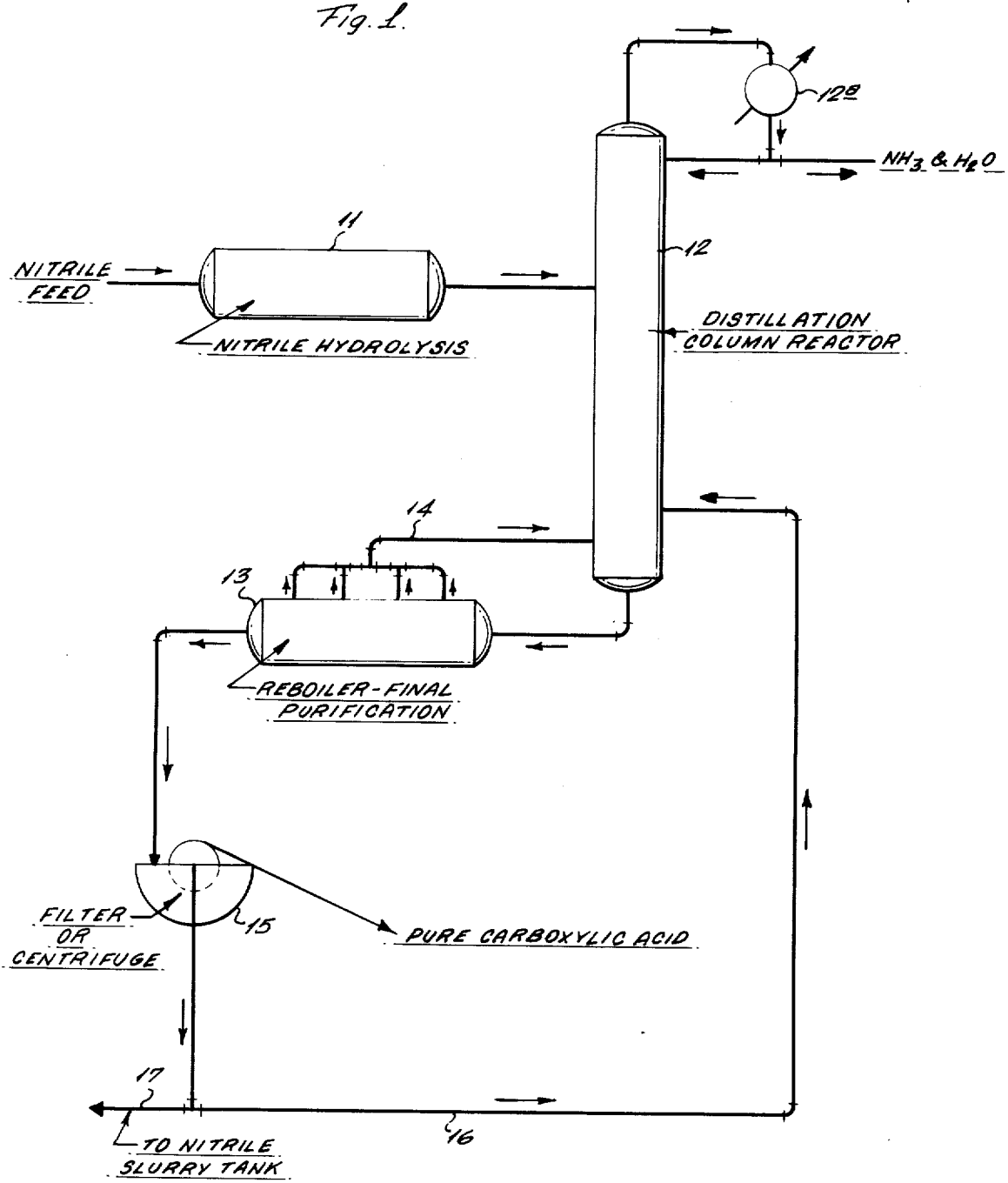
FIG. 1 is a flow diagram to illustrate the overall process.

To explain the invention more fully reference is now made to FIG. 1 where the preferred process will be illustrated with a hydrolyzate of terephthalonitrile. The terephthalonitrile to be hydrolyzed is fed into a closed hydrolytic chamber (11) where hydrolysis occurs at a temperature between about 200° and about 325° C. under autogeneous pressure, the pressure actually rising to about 220° to about 1740 psia. In this reactor, the hydrolysis proceeds until an equilibrium is reached which at the preferred range of about 250° C. to about 325° C. requires from about 2 to about 0.1 hours. The hydrolysis products in the equilibrium mixture as shown above, will consist essentially of the diammonium salt of terephthalic acid and ammonium terephthalamate together with small amounts of the ammonium salt of 4-cyanobenzoic acid, 4-cyanobenzamide, and terephthalamide. After the equilibrium is established, the aqueous mixture is fed into a reactive distillation column (12) where hydrolysis of nitrogen-containing aromatics occurs in a stripping section of the column and concentration of the resulting ammonia occurs in the upper section. It is in this way that the equilibrium is shifted by removal of ammonia taken overhead together with water vapor. The drawing shows a preferred method of handling the overhead by passing it through a partial condenser (12a) and returning the condensate to reflux. The reactor column is operated at a temperature between about 200° C. and about 325° C. preferably about 260° C. to about 310° C. and at autogenous pressure which will be a pressure of between abouut 220° and about 1750 psia. It is important that the residence time of materials within the column be longer than that found in simple distillation systems and a preferred method to accomplish an increased residence time is by means of the apparatus disclosed in the copending application of Allen W. Hancock II, Ser. No. 463,493, filed Apr. 24, 1974, now abandoned, which employs liquid reservoirs between trays within the column. In the process of this invention residence time will be preferably between about 15 and about 45 minutes and these long residence times are necessary to provide time to enable the hydrolysis equilibrium system to be shifted from the amides toward the salts as the ammonia is removed. To separate the ammonia effectively, only moderate reflux ratios on the order of 2 to 10 are required. A particular advantage of this portion of the process is that the actual water carried over is only a small fraction of the water in the feed. Thus, for example, a typical feed concentration to the column reactor may contain one mole of aromatic material to 50 moles of water and, even if the mole percent of water in the overhead is quite high (e.g., 50 mole %), the actual quantity of water carried over is only a small fraction of the feed (about 4%). Likewise, the ammonia is significantly concentrated. For example, the ammonia concentration of the hydrolysate input is about 4 mole percent, but after concentration by rectification in the column it exits at no less than about 50 mole percent. Furthermore, there is no carryover of aromatic compounds in the overhead. It is thus clear that one major advantage of the process is that the utility requirements are low and thus a highly efficient process is achieved. This is in contrast to known techniques where ammonia is removed by steam sweeping which often requires that the quantity of steam be that or approach that of the feed itself and this high steam volume mitigates against an economical process.

The terephthalic acid product which flows to the bottom of the column is taken to a reboiler (13) where any residual intermediate materials are further converted by hydrolysis and removal of ammonia to terephthalic acid. The ammonia that is generated by this hydrolysis is returned to the column through line 14 where it is eliminated with the overhead stream. Residence time in the reboiler is about 0.5 to 3 hours and it is this relatively long residence time in the reboiler together with the low concentration of organics therein that enables the improved product purity to be obtained. It will be understood that although the reboiler (13) is shown separate from the distillation column (12), the reboiler may be an integral part of the bottom portion of the column as is frequently the case with industrial equipment. The solution of high purity terephthalic acid thus obtained is taken from the reboiler, cooled and separated by filtration, centrifugation or other conventional means (15) and pure crystals of the aromatic acid are obtained. The filtrate from the separation step is taken through line 16 back to a lower portion of the column (12) and preferably fed into the column through a series of inputs in a manifold type arrangement so as to ensure distillation of the liquid over a relatively large area within the lower section of the column. A portion of the filtrate as shown in line 17 may, if desired, be returned to the nitrile slurry tank which feeds the nitrile hydrolyzer.

Figure 3:
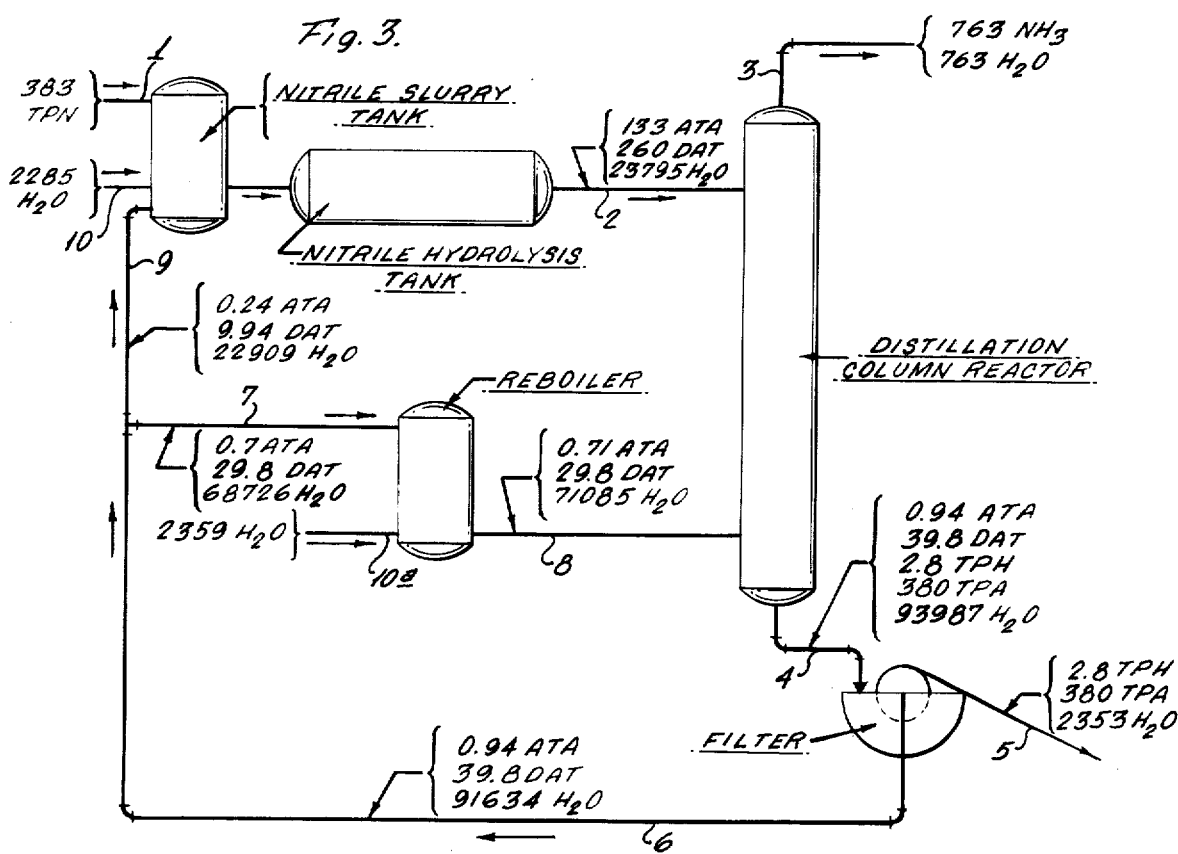
FIG. 3 is a flow diagram of the process of the invention showing molar flows.

In feeding the filtrate to the lower portion of the distillation column, the diluent will be introduced into about the lower third of the column and will preferably be fed into about the lower tenth of the column. However, it is to be understood that the lower portion of the column includes the reboiler and the diluent may be fed directly to the reboiler to achieve desirable results as is shown in FIG. 3.

The return of the filtrate to the lower portion of the column (12) as described above makes a significant contribution to the process in that the purity of the product is greatly enhanced without loss of process efficiency. That is, the amount of any unreacted amide in the product is significantly reduced without adversely affecting removal of ammonia in the upper portion of the column. This can be seen in FIG. 4 where the amide nitrogen content of the column bottoms products (e.g., line 4 of FIG. 3 illustrated with terephthalic acid) is plotted against the concentration of total aromatics in the system. As can be seen, as the aromatics concentration is reduced, the nitrogen content in the product drops. The process of the invention has a further advantage in that it enables the column (12) to be operated with a smaller number of stages (e.g., plates) in order to achieve a given purity level.

To further exemplify the process of the invention and the results obtained thereby, the following examples are given.

Example 1 (Control)

Figure 2:
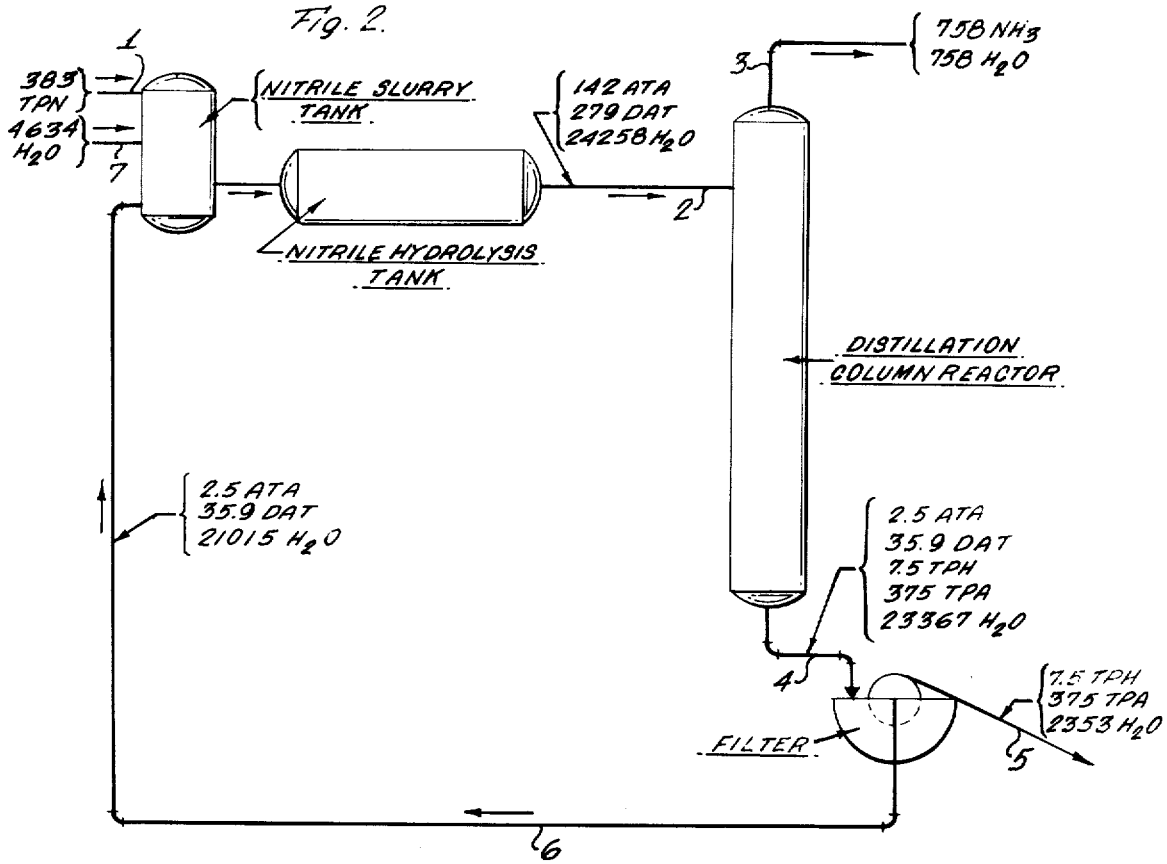
FIG. 2 is a flow diagram showing a control process not embodying the process of the invention, but showing molar balance of the system.

FIG. 2 illustrates a control process not embodying the recycle step of the invention and shows a flow diagram and molar balance for a terephthalic acid plant having a capacity of 500 million pounds per year. The material balance showing the component composition of the streams numerically identified in FIG. 2 is given in the following Table I.

TABLE I

MATERIAL BALANCE FOR PROCESS OF FIGURE 2
Plant Capacity - 500 mm lbs./yr.
Component flows in lbs/hr.

| Component | Stream 1 | Stream 2 | Stream 3 | Stream 4 | Stream 5 | Stream 6 | Stream 7 |
|---|---|---|---|---|---|---|---|
| TPN | 48982.2 | — | — | — | — | — | — |
| ATA | — | 25894.9 | — | 454.4 | — | 454.4 | — |
| DAT | — | 55750.7 | — | 7172.7 | — | 7172.7 | — |
| TPH | — | — | — | 1235.9 | 1235.9 | — | — |
| TPA | — | — | — | 62280.4 | 62280.4 | — | — |
| $NH_3$ | — | — | 12883.6 | — | — | — | — |
| $H_2O$ | — | 436635.3 | 13641.5 | 420612.5 | 42347.3 | 378265.2 | 83406.4 |
| Total | 48982.2 | 518280.9 | 26525.1 | 491755.9 | 105863.6 | 385892.3 | 83406.4 |

Legend:
TPN = Terephthalonitrile
ATA = Ammonium Terephthalamate
DAT = Diammonium Terephthalate
TPH = Terethalamic Acid
TPA = Terephthalic Acid

EXAMPLE 2

FIG. 3 illustrates a flow diagram of the process of the invention and shows molar flows. Table II which follows shows the component compositions of the various streams shown in FIG. 3.

Table III compares the amide nitrogen levels of column feed, (stream 2), bottoms product (stream 4), and product acid (stream 5) as well as percent conversion of amide nitrogen to acid. As can be seen, the process of the invention gives a significant improvement in product purity over the control.

TABLE II

MATERIAL BALANCE FOR PROCESS OF FIGURE 3
Plant Capacity - 500 mm lbs/yr
Component Flows in lbs/hr.

| Component | Stream 1 | Stream 2 | Stream 3 | Stream 4 | Stream 5 | Stream 6 | Stream 7 |
|---|---|---|---|---|---|---|---|
| TPN | 48982.2 | — | — | — | — | — | — |
| ATA | — | 24161.2 | — | 171.3 | — | 171.3 | 128.4 |
| DAT | — | 52018.5 | — | 7950.0 | — | 7950.0 | 5962.5 |
| TPH | — | — | — | 465.9 | 465.9 | — | — |
| TPA | — | — | — | 63055.1 | 63055.1 | — | — |
| $NH_3$ | — | — | 12962.9 | — | — | — | — |
| $H_2O$ | — | 428301.5 | 13725.4 | 1691764.2 | 42347.3 | 1649416.9 | 1237062.7 |
| Total | 48982.2 | 504481.2 | 26688.3 | 1763406.4 | 105868.3 | 1657538.1 | 1243153.6 |

| Component | Stream 8 | Stream 9 | Stream 10 | Stream 10a |
|---|---|---|---|---|
| TPN | — | — | — | — |
| ATA | 128.4 | 42.8 | — | — |
| DAT | 5962.5 | 187.5 | — | — |
| TPH | — | — | — | — |
| TPA | — | — | — | — |
| $NH_3$ | — | — | — | — |
| $H_2$ | 1279522.6 | 412354.2 | 41130.7 | 42459.9 |

TABLE II-continued

MATERIAL BALANCE FOR PROCESS OF FIGURE 3
Plant Capacity - 500 mm lbs/yr
Component Flows in lbs/hr.

| | | | | |
|---|---|---|---|---|
| Total | 1285613.5 | 412584.5 | 41130.7 | 42459.9 |

TABLE III

Amide Nitrogen Levels (ppm)

| | Example 1 | Example 2 |
|---|---|---|
| Column Feed (Stream 2) -: | 28,500 | 28,500 |
| Bottoms Product (Stream 4) -: | 2,000 | 750 |
| Product TPA (Stream 5) -: | 1,651 | 622 |
| Conversion of Amide Nitrogen to TPA -: | 94.2% | 97.8% |

The invention claimed is:

1. In the process for making an aromatic carboxylic acid of high purity by feeding an essentially equilibrium hydrolysis mixture of an aromatic nitrile to a reactive distillation column operated at a temperature of from about 200° C. to about 325° C. at autogenous pressure where the equilibrium mixture is subjected simultaneously to further hydrolysis and distillation of ammonia, removing water vapor and ammonia from the top of the column, subjecting remaining equilibrium hydrolysis mixture to further hydrolysis and distillation in a reboiler, returning vapor from the reboiler to the distillation column, removing an aqueous solution of product acid from the reboiler, cooling said separated solution, and separating aromatic acid product, the improvement of returning the aqueous filtrate from said separate aromatic acid product to a lower portion of said column whereby product purity is enhanced.

2. The process of claim 1 where the aromatic nitrile is benzonitrile.

3. The process of claim 1 where the aromatic nitrile is a phthalonitrile.

4. The process of claim 3 where the phthalonitrile is terephthalonitrile.

5. The process of claim 3 where the nitrile is isophthalonitrile.

6. The process of claim 1 where the nitrile is a naphthalonitrile.

7. The process of claim 6 where the naphthanitrile is 2,6-dicyanonaphthalene.

8. In the process for making an aromatic carboxylic acid of high purity from the hydrolysate of the corresponding nitrile obtained by ammoxidation of an alkyl aromatic compound by hydrolyzing an aromatic nitrile of the benzene or naphthalene series in a closed reactor at a temperature of from about 200° C. to about 325° C. until an essentially complete hydrolysis equilibrium is obtained, feeding said essentially equilibrium hydrolysis mixture of said aromatic nitrile to a reactive distillation column operated at a temperature of from about 200° C. to about 325° C. and at autogenous pressure where the equilibrium mixture is subjected simultaneously to further hydrolysis and distillation of ammonia, concentrating ammonia by rectification in the upper portion of the column, removing the concentrated aqueous ammonia vapor from the top of the column, subjecting the remaining equilibrium hydrolysis mixture to further hydrolysis and distillation in a reboiler operated at about 200° C. to about 325° C., returning vapors from the reboiler to a lower portion of the distillation column, removing an aqueous solution of product from the reboiler, cooling said separated solution, and separating aromatic acid product the improvement of returning the aqueous filtrate from said separated aromatic acid product to a lower portion of said column whereby product purity is enhanced.

9. The process of claim 8 where the nitrile is terephthalonitrile obtained by ammoxidation of p-xylene.

10. The process of claim 8 where the nitrile is isophthalonitrile obtained by ammoxidation of m-xylene.

11. The process of claim 8 where the nitrile is 2,6-dicyanonaphthalene obtained by ammoxidation of 2,6-dimethylnaphthalene.

12. In the process for making an aromatic carboxylic acid of high purity by feeding an essentially equilibrium hydrolysis mixture of an aromatic nitrile to a reactive distillation column operated at a temperature of from about 200° C. to about 325° C. at autogenous pressure where the equilibrium mixture is subjected simultaneously to further hydrolysis and distillation of ammonia, removing water vapor and ammonia from the top of the column, subjecting remaining equilibrium hydrolysis mixture to further hydrolysis mixture to further hydrolysis and distillation in a reboiler, returning vapor from the reboiler to the distillation column, removing an aqueous solution of product acid from the reboiler, cooling said separated solution, and separating aromatic acid product, the improvement of maintaining within said column a concentration gradient of its organic components such that the lower portion of the column is more dilute than the upper portion, whereby purity of the aromatic acid product is enhanced.

* * * * *